United States Patent
Brandhorst et al.

(10) Patent No.: US 6,302,690 B1
(45) Date of Patent: Oct. 16, 2001

(54) DENTAL IMPRESSION TRAY

(75) Inventors: Gerd Brandhorst, Landsberg; Johann Fetz, Windach; Ingo Wagner, Herrsching; Joachim Zech, Seefeld, all of (DE)

(73) Assignee: ESPE Dental AG, Seefeld (DE)

( * ) Notice: Subject to any disclaimer, the term of this patent is extended or adjusted under 35 U.S.C. 154(b) by 0 days.

(21) Appl. No.: 09/656,024

(22) Filed: Sep. 6, 2000

(30) Foreign Application Priority Data

Sep. 8, 1999 (DE) .............................................. 199 42 917

(51) Int. Cl.$^7$ ..................................................... A61C 9/00
(52) U.S. Cl. ................................. 433/45; 433/37; 433/41
(58) Field of Search ................................. 433/34, 37, 41, 433/45, 47

(56) References Cited

U.S. PATENT DOCUMENTS

| | | | | |
|---|---|---|---|---|
| 1,611,201 | * | 12/1926 | Kidder | 433/45 |
| 2,529,429 | * | 11/1950 | Spiro | 433/41 |
| 3,056,205 | * | 10/1962 | Ennor | 433/37 X |
| 4,375,965 | * | 3/1983 | Weissman | 433/37 |
| 5,551,872 | * | 9/1996 | Mena | 433/41 |

* cited by examiner

*Primary Examiner*—Nicholas D. Lucchesi
(74) *Attorney, Agent, or Firm*—Connolly Bove Lodge & Hutz

(57) ABSTRACT

A dental impression tray comprises a mold shell made of synthetic material and having an inner space for receiving the impression material, and a support shell made of metal and surrounding the exterior of the mold shell in order to provide the overall impression tray with the rigidity and dimensional stability required for taking precisely fitting impressions. The support shell may be detachably connected to the mold shell by positive or non-positive engagement. While the mold shell including the impression material is passed on to the technician who will produce a model of the teeth from which the impression was taken and who may subsequently dispose of the mold shell including the impression material, the support shell will remain with the dentist, immediately ready for reuse upon sterilization.

17 Claims, 3 Drawing Sheets

DENTAL IMPRESSION TRAY

BACKGROUND OF THE INVENTION

Dental impression trays serve to receive a curable material to obtain an impression of a patient's tooth or teeth. By filling the impression, e.g. with gypsum or other materials, a model of the tooth or teeth can be produced which may serve as the working basis for the dental technician.

The precision of the impression is of critical importance for producing high-quality, well fitting dental replacement parts.

Known in the art are impression trays of metal and of synthetic material. Both are widely in use.

Due to the varying sizes and geometries of the human jaws and depending on the specific application, a plurality of tray sizes and shapes, often sold in sets, must be available. Further, since the most frequently needed trays are most frequently with the technician, a plurality of sets of trays must be available to the dentist.

Impression trays of metal are of advantage as their high rigidity and dimensional stability permits the production of very exact impressions and models, from which very exactly fitting dental replacement parts can be prepared. Due to the necessity of having a plurality of sets of trays, the use of metal trays involves high costs. In view of the high costs, the dentist is further faced with the inconvenience of having to control the return of the metal trays from the technician or dental laboratory. In addition, the dentist has to provide for suitable storage of metal trays upon their sterilization to exclude contamination until their reuse.

Another essential disadvantage of metal impression trays resides in the fact that they cannot be individualized. In contrast to trays of materials such as synthetic resin, which can be worked easily, metal trays are unsuited for adapting the tray geometry to the anatomy of an individual patient.

Impression trays of synthetic material, on the other hand, involve low cost and therefore permit disposal. They further allow the cured model to be removed by destroying the tray, which may be useful with certain impressions, e.g., in the case of undercuts, in order to save the model. Furthermore, there is no sterilization and subsequent clean storage. However, the relatively low mechanical strength and dimensional stability of trays made of synthetic material may lead to deformations of the impression while taken. Models prepared from a deformed impression are less accurate and thus of lower quality. If the dimensions of the model differ from those of the teeth from which it was taken, imperfect fitting of the finished dental replacement part will result even if the technician has worked meticulously from the model. In such a case, post-treatment by the dentist will be necessary, if at all possible, and the patient will end up with a dental replacement part that does not fit completely.

German Offenlegungsschrift 196 28 682 discloses a reusable metallic dental impression tray made of several parts that can be disassembled to simplify the removal of the cured impression material.

German Patent Specification 4131 145 shows a dental impression tray made of metal with a thin, flexible insert made of plastic material. Both parts cooperate to receive the impression material and form retentions therefor. Since the flexible insert has virtually no rigidity of its own, it must be supported on all sides by the outer tray.

SUMMARY OF THE INVENTION

It is an object of the present invention to provide a dental impression tray which has high overall mechanical strength and dimensional stability without involving high investment or storage costs.

This object is met by a dental impression tray comprising an inner mold shell defining a space for receiving an impression material, and an outer support shell surrounding and supporting the mold shell, the mold shell being completely closed with respect to the support shell to constitute the sole means for receiving impression material.

The object is also met by a dental impression tray comprising an inner mold shell having a peripheral wall and a bottom, the peripheral wall and a bottom defining a space for receiving an impression material, and an outer support shell surrounding and supporting the mold shell substantially only along the peripheral wall.

While the mold shell constitutes the only receptacle for the impression material, the support shell serves to provide the mold shell with sufficient dimensional stability to avoid deformations when the impression is being taken, and also when the tray with the uncured impression material is withdrawn from the teeth and during the curing of the material. While the support shell is reused, the mold shell may be discarded after removal of the cured model by the technician.

The two-part structure of the impression tray has the further advantage that the dentist requires only a small number of differently sized and shaped metal support shells since the exact shape of the space receiving the impression material is determined by the mold shell, and since it is possible 5 to use several different mold shells in combination with one support shell.

The support shell of the present invention can be used for both an upper jaw and a lower jaw. Conventionally, impression trays for upper jaws often differ from those for lower jaws in that the former ones have a palatine plate which does not exist with the latter ones. With the impression tray of the present invention, a support shell with no palatine plate can be used in combination with mold shells for upper jaws and mold shells for lower jaws.

Thus, the number of support shells which a dentist must have available is limited in that it is only necessary to meet different sizes and shapes of human teeth. The technician and dental lab require only one set of support shells to hold the mold shells filled with impression material, no sterilization or cleaning being necessary.

In a preferred embodiment, the mold shell and the support shell are made of different materials; preferably, the mold shell is made of synthetic material and the support shell is made of metal. In this manner, the advantages of a metal impression tray are combined with those of a plastic one without the disadvantages of either.

In another preferred embodiment, the mold shell and the support shell are adapted to be detachably connected by positively engaging means. Preferably, the mold shell and the support shell are provided with slidably engaging means. The support shell may have a peripheral wall, an inner side of which is provided with a groove for engagement with an outward projecting flange provide on the mold shell. Further, the mold shell may have a peripheral wall provided with an outward extending flange for engagement with the free outer edge of the peripheral wall provided on the support shell. Further, the mold and support shells may be provided with mutually engaging locking means.

All these structural features achieve a mechanically strong, yet releasable engagement between the support and mold shells, thus permitting the production of precisely fitting dental replacement parts.

In accordance with another embodiment of the invention, the support shell has a peripheral wall provided with an opening, and the mold shell has an outward projection adapted to extend through the opening and engage an outer portion of the support shell. The extension may be formed by a stock provided with a detent nose spaced from the peripheral wall of the mold shell, for engagement with a step provided on a handle or the support shell. In this embodiment, the impression tray is particularly easy and safe to disassemble without impairing the quality of the impression.

In another preferred embodiment, the mold shell has retention means for engagement with the impression material. Suitable retention structures or shown in U.S. Pat. Nos. 5,772,432 and 5,890,895 and in WO 97/32537.

Further, the inner surface of the mold shell may be provided with a self-adhesive substance or a self-adhesive sheet of woven or non-woven material. This saves the dentist most of the preparatory work necessary with many prior art impression trays which must be coated with an adhesive substance before they can be filled with the impression material.

DETAILED DESCRIPTION OF PREFERRED EMBODIMENTS

Figure 1:
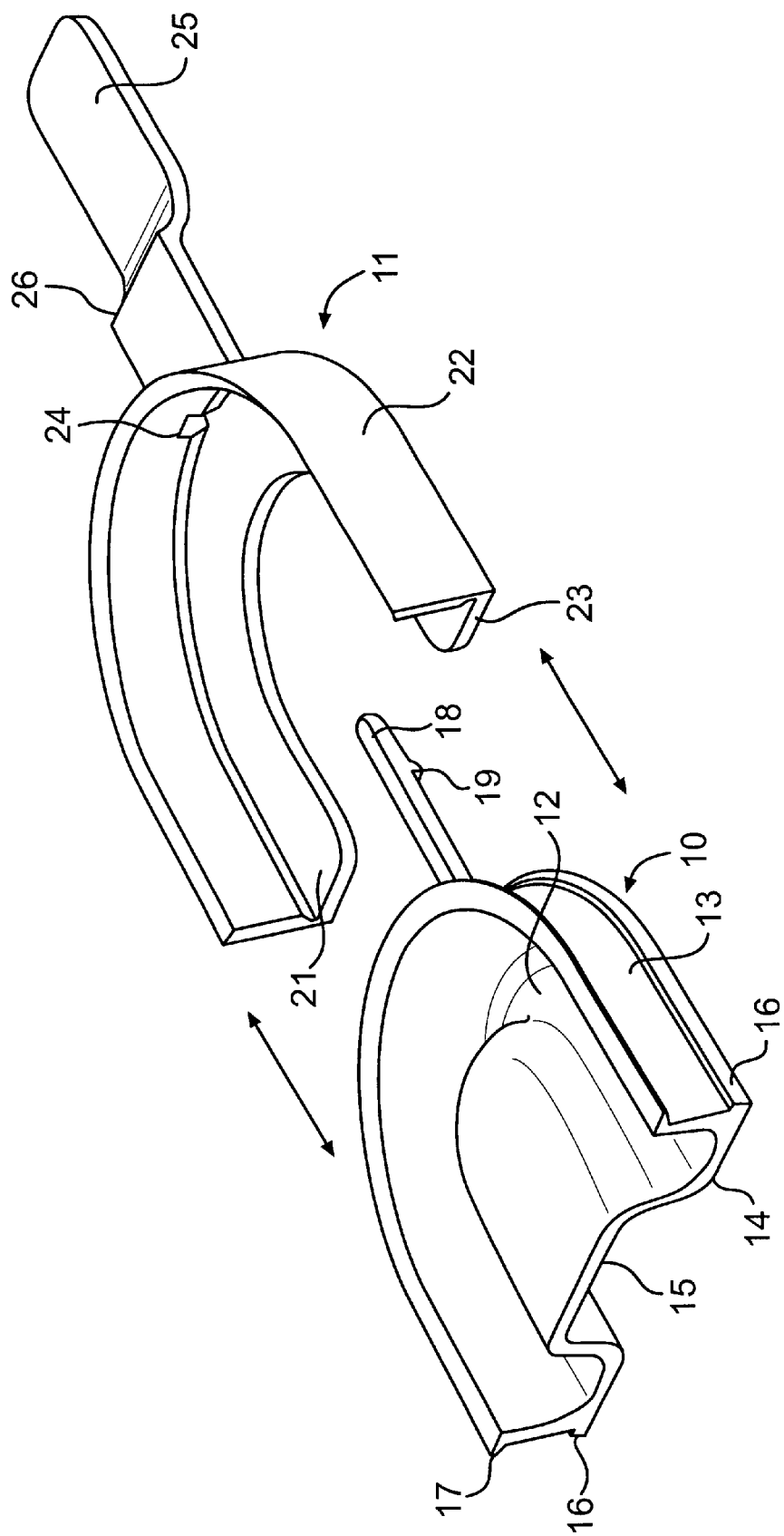
FIG. 1 is a perspective exploded view of a dental impression tray for an upper jaw, with the mold shell and support shell being shown separated from each other.

In accordance with FIG. 1, the dental impression tray consists of a mold shell 10 made of synthetic material and a support shell 11 made of metal. The mold shell defines a somewhat semi-annular open top space 12 of a size and shape roughly corresponding to an upper jaw, for receiving a dental impression material (not shown).

The space 12 is confined by a peripheral wall 13 and a bottom 14 the inner portion 15 of which is upwardly curved. The inner portion 15 constitutes a palatine plate which is present only with impression trays for the upper jaw; it does not exist with trays for the lower jaw.

A radially outward extending flange 16 is formed integrally with the lower edge of the peripheral wall 13, and a radially outward extending upper flange 17 is formed integrally with the free upper edge of the peripheral wall 13.

A stock 18 extends from the lower flange 16 of the mold shell 10 at the rear in FIG. 1 and is provided with a downward extending detent nose 19 spaced from the outer side of the peripheral wall 13.

The support shell 11 has a semi-annular bottom 21, the outer side of which is surrounded by a peripheral wall 22. A groove 23 extends along the line of transition between the bottom 21 and the peripheral wall 22, the groove 23 being complementary to the lower flange 16 of the mold shell 10. The peripheral wall 22 of the support shell 11 is provided with an opening 24 at the rear center, as seen in FIG. 1, through which the stock 18 of the mold shell 10 may be passed.

The support shell 11 is provided with an rearward extending handle 25 formed integrally with the outer side of the peripheral wall 22. A central portion of the handle 25 is bent to form a rectangular step 26.

Before use, the mold shell 10 is so inserted into the support shell 11 that the lower flange 16 of the mold shell 10 engages the groove 23 of the support shell 11 and the stock 18 penetrates the opening 24. In the completely assembled condition, the nose 19 audibly and sensibly snap-locks behind the step 26 formed in the handle 25.

The peripheral wall 22 of the support shell 11 has a height which is so dimensioned that the upper flange 17 of the mold shell 10 fits over the upper end of the peripheral wall 22.

Figure 2:
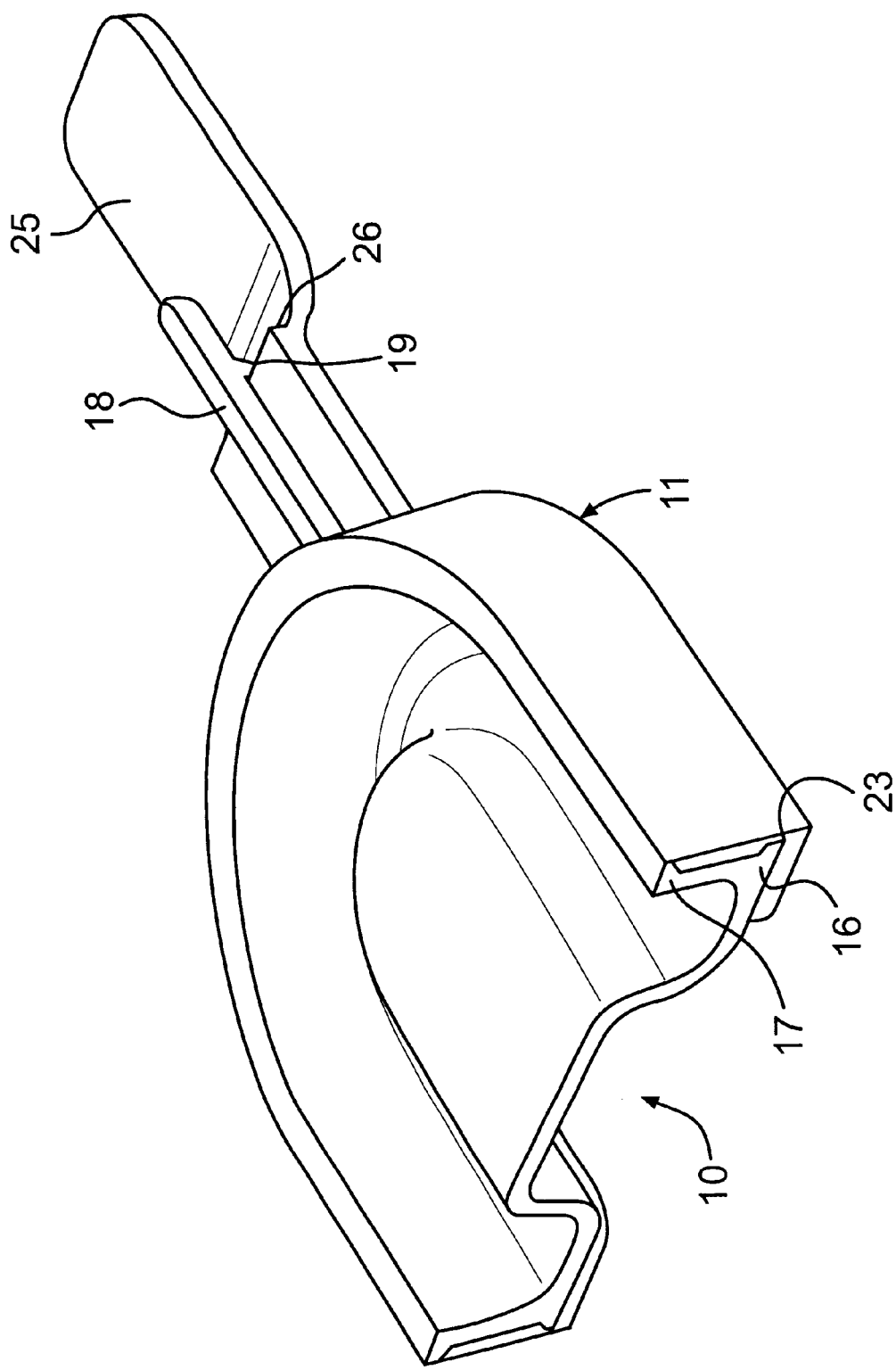
FIG. 2 shows the impression tray of FIG. 1 in its assembled and locked condition.

In this condition, which is shown in FIG. 2, the upper surface of the bottom 21 of the support shell 11 closely abuts the lower side of the annular bottom 14 of the mold shell 10 in such a manner that part of the bottom 14 and the entire peripheral wall 13 of the mold shell 10 are surrounded and supported by the support shell 11.

The mold shell of the thus assembled impression tray can now be filled with impression material and pressed onto a patient's teeth so that a negative of the teeth will be formed in the material. At this time, and when the tray with the still uncured impression material is withdrawn from the teeth, the metal support shell 11 prevents deformations of the less rigid plastic mold shell 10.

Although the drawing shows the bottom 21 of the support shell 11 as having a radial width almost the same as that of the lowermost part of the bottom 14 of the mold shell 10, it has been found that it is only necessary for the bottom 21 to be wide enough to prevent the mold shell 10 from moving axially. In other words, for properly supporting and reinforcing the mold shell 10 during the taking of impressions, it is sufficient for the support shell 11 to surround and support substantially only the peripheral wall 13 of the mold shell 10.

Upon withdrawal from the patient's mouth, the mold shell 10 is separated from the support shell 11 by lifting the outer part of the stock 18 from the handle 25 until the detent nose 19 may be slid over the step 26 and the mold shell 10 can be moved out of the support shell 11.

Due to the rather large distance between the nose 19 and the peripheral wall 13 of the mold shell 10, the locking between the nose 19 and the step 26 can be released by a relatively small force. At the same time, this distance in combination with the fact that the stock 18 extends through the relatively narrow opening 24 in the peripheral wall 22 of the support shell 11, results in the advantage that movements of the stock 18, which is formed integrally with the mold shell 10, do not cause distortions of the inner space 12 of the mold shell 10 which holds the impression material. This in turn prevents the impression from becoming distorted.

The mold shell 10 including the cured impression material is then handed over to the technician who can easily remove the material from the mold shell. In doing so, he may destroy the mold shell 10 if necessary to avoid damages on the model—as may be caused by existing undercuts. In any case, no cleaning of the mold shell 10 is required. It is only the metallic support shell 11 which remains with the dentist and, upon sterilization, is immediately available for reuse.

The mold shell 10 may have its interior side coated with a self-adhesive substance. Alternatively, it can be provided with a self-adhesive sheet of woven or non-woven material to ensure a strong holding force on the molding material by micro-retention. Since it is not necessary for the dentist to apply an adhesive to the mold shell 10, the time he has to spend to prepare an impression tray is shortened. If the dentist, for correction purposes, wishes to take a second impression, he may remove the first impression material from the mold shell 10 at which time the retentive microfibers of the adhesive sheet will be re-raised due to the first material being torn off, so that the second impression material will again be retained safely.

Figure 3:
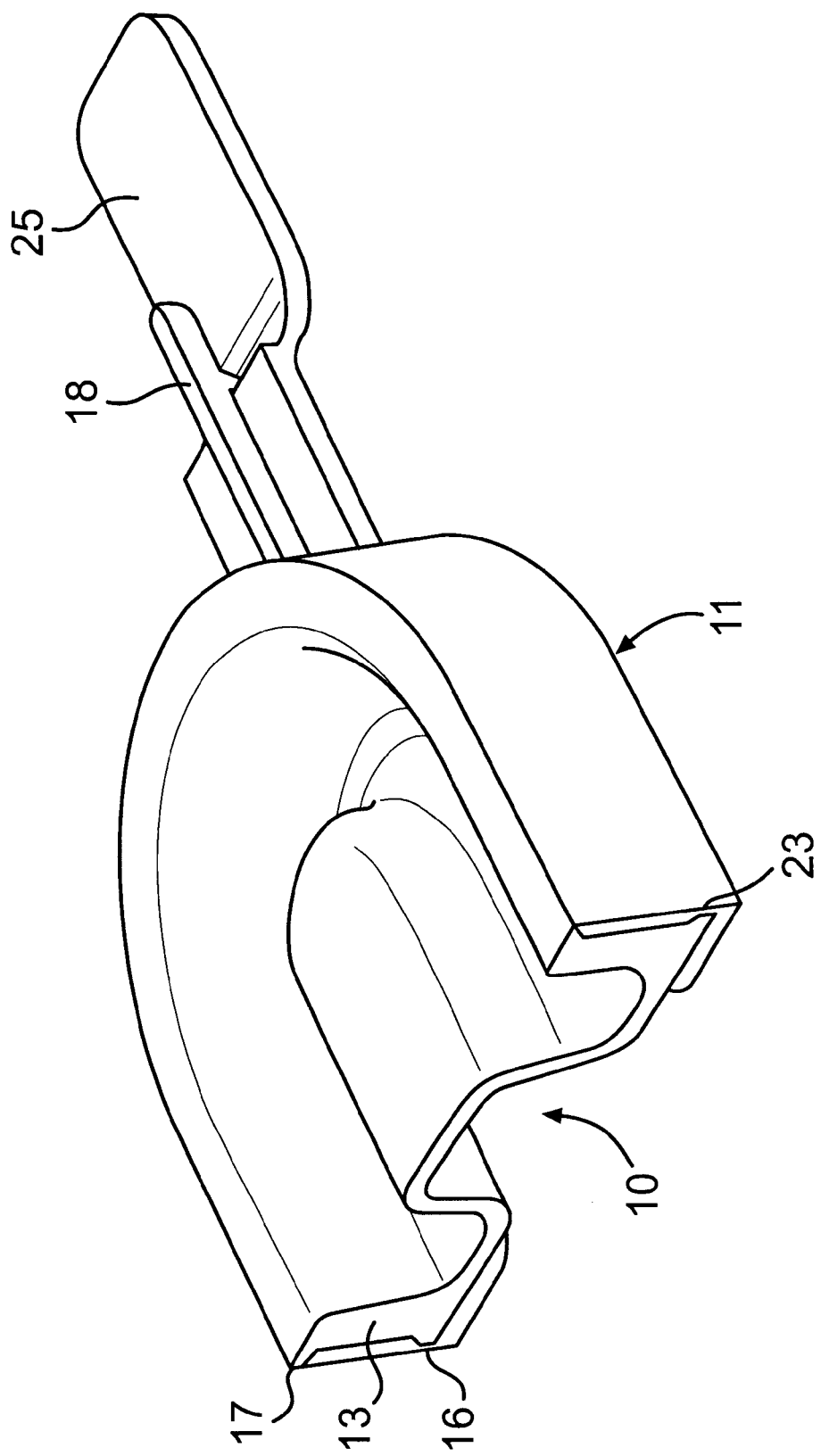
FIG. 3 is a representation similar to FIG. 1, showing how a mold shell having a different inner size and shape may be used in connection with the same support shell.

FIG. 3 shows the same support shell 11 as FIGS. 1 and 2 but in connection with a mold shell 10' which differs from the mold shell 10 of in that its peripheral wall 13' has a larger thickness with an identical outer shape. By this change in wall thickness which, as a further alternative, may vary along the length of the peripheral wall, a plurality of mold shells 10, 10' of different shapes and sizes may be used with the same support shell 11. This reduces the number of different, expensive metallic impression trays or support shells which a dentist must have available.

What is claimed is:

1. A dental impression tray comprising an inner mold shell defining a space for receiving an impression material, an outer support shell surrounding and supporting an outer side of said mold shell, and engaging means for connecting said mold shell and said support shell so as to prevent relative movement between said mold shell and said support shell during the taking of an impression, said mold shell being completely closed with respect to said support shell so that said mold shell constitutes the sole means to receive impression material.

2. The dental impression tray of claim 1 wherein said mold shell and said support shell are made of different materials.

3. The dental impression tray of claim 2, wherein said mold shell is made of synthetic material and said support shell is made of metal.

4. The dental impression tray of claim 1, wherein said engaging means are adapted to detachably connect said mold shell and said support shell.

5. The dental impression tray of claim 4, wherein said engaging means are adapted to slidably connect said mold shell and said support shell.

6. The dental impression tray of claim 5 wherein said support shell has a peripheral wall, an inner side of which is provided with a groove, and said mold shell has an outward projecting flange for engagement with said groove.

7. The dental impression tray of claim 6 wherein said mold shell has a peripheral wall provided with an outward extending flange, and said peripheral wall of said support shell has a free outer edge adapted to be engaged by said flange provided on the peripheral wall of said mold shell.

8. The dental impression tray of claim 4 wherein said mold shell and said support shell are provided with locking means adapted to engage each other in a completely assembled condition of said mold shell and support shell.

9. The dental impression tray of claim 8 wherein said support shell has a peripheral wall provided with an opening, and said mold shell has an outward projection adapted to extend through said opening and engage an outer portion of said support shell.

10. The dental impression tray of claim 9 wherein said extension is formed by a stock provided with a detent nose spaced from said peripheral wall of said mold shell, and said support shell has a handle provided with a step adapted for engagement by said detent nose.

11. The dental impression tray of claim 1 wherein said mold shell has retention means for engagement with said impression material.

12. The dental impression tray of claim 11 wherein said mold shell has an inner surface provided with a self-adhesive substance.

13. The dental impression tray of claim 11 wherein said mold shell has an inner surface provided with a self-adhesive sheet.

14. The dental impression tray of claim 13 wherein said sheet is made of non-woven material.

15. A dental impression tray having an outer side provided with means for positively and detachably engaging an outer support shell, said tray alone defining a space as the only means for receiving impression material.

16. A set of dental impression trays comprising a support shell as defined in claim 1 and a plurality of differently shaped mold shells as defined in claim 1.

17. A dental impression tray according to claim 1, said mold shell having a peripheral wall and a bottom which define said space for receiving an impression material, and said outer support shell surrounding and supporting said mold shell substantially only along said peripheral wall.

* * * * *